(12) United States Patent
Pitarresi et al.

(10) Patent No.: US 10,709,787 B2
(45) Date of Patent: Jul. 14, 2020

(54) HYDROGELS OF METHACRYLIC HYALURONIC ACID DERIVATIVES FOR ORAL ENZYME THERAPY IN CELIAC DISEASE

(71) Applicant: Nemysis Limited, Dublin (IE)

(72) Inventors: Giovanna Pitarresi, Palermo (IT); Fabio Salvatore Palumbo, Trabia (IT); Gaetano Giammona, Palermo (IT)

(73) Assignee: NEMYSIS LIMITED, Dublin (IE)

( * ) Notice: Subject to any disclaimer, the term of this patent is extended or adjusted under 35 U.S.C. 154(b) by 250 days.

(21) Appl. No.: 15/307,790

(22) PCT Filed: May 6, 2015

(86) PCT No.: PCT/EP2015/059941
§ 371 (c)(1),
(2) Date: Oct. 28, 2016

(87) PCT Pub. No.: WO2015/169849
PCT Pub. Date: Nov. 12, 2015

(65) Prior Publication Data
US 2017/0049896 A1   Feb. 23, 2017

(30) Foreign Application Priority Data

May 7, 2014 (IT) .............. FI2014A0106

(51) Int. Cl.
| | |
|---|---|
| A61K 47/36 | (2006.01) |
| C08J 3/28 | (2006.01) |
| A61K 38/48 | (2006.01) |
| A61K 9/19 | (2006.01) |
| A61K 9/20 | (2006.01) |
| C08B 37/08 | (2006.01) |
| C08L 5/08 | (2006.01) |
| A61K 9/00 | (2006.01) |
| A61K 9/06 | (2006.01) |
| A61K 47/14 | (2017.01) |
| A61K 47/18 | (2017.01) |
| A61K 47/26 | (2006.01) |
| C08J 3/24 | (2006.01) |

(52) U.S. Cl.
CPC ............ *A61K 47/36* (2013.01); *A61K 9/0053* (2013.01); *A61K 9/06* (2013.01); *A61K 9/19* (2013.01); *A61K 9/205* (2013.01); *A61K 38/482* (2013.01); *A61K 47/14* (2013.01); *A61K 47/18* (2013.01); *A61K 47/26* (2013.01); *C08B 37/0072* (2013.01); *C08J 3/24* (2013.01); *C08J 3/28* (2013.01); *C08L 5/08* (2013.01); *C12Y 304/21026* (2013.01); *C08J 2305/08* (2013.01)

(58) Field of Classification Search
CPC ........ A61K 47/36; A61K 38/482; A61K 9/19; C08J 3/28
See application file for complete search history.

(56) References Cited

U.S. PATENT DOCUMENTS

2011/0236486 A1* 9/2011 Giammona .............. B23K 9/10
424/488

FOREIGN PATENT DOCUMENTS

| WO | WO2007044906 | 4/2007 |
| WO | WO2010061005 | 6/2010 |

OTHER PUBLICATIONS

Colaco et al., Chemistry of protein stabilization by trehalose, American CHemical Society, Ch. 14, p. 222-240 (Year: 1994).*
Jain et al., Effect of trehalose on protein structure, Protein Science, vol. 18, p. 24-36 (Year: 2009).*
Satish et al., Hydrogels as controlled drug delivery systems: synthesis, crosslinking, water and drug transport mechanism, Indian Journal of Pharmaceutical Sciences, vol. 68, p. 133-140. (Year: 2006).*
Pitaressi et al., Photo-cross-linked hydrogels with polysaccharide-poly(amino acid) structure: new biomaterials for pharmaceutical applications, Biomacromolecules, vol. 7, p. 1302-1310. (Year: 2006).*
Calogero Fiorica, et al; "A New Hyaluronic Acid pH Sensitive Derivative Obtained by ATRP for Potential Oral Administration of Proteins"; International Journal of Pharmaceutics; 2013; p. 150-157.

* cited by examiner

*Primary Examiner* — Taeyoon Kim
*Assistant Examiner* — Tiffany M Gough
(74) *Attorney, Agent, or Firm* — Stetina Brunda Garred and Brucker (57) ABSTRACT

The present invention relates to a composition comprising hydrogels from functionalized hyaluronic acid derivatives, said hydrogels loaded with exogenous enzymes selected in the group consisting of prolyl endopeptidase (PEP) and endoprotease (EP) intended for the oral treatment of celiac disease. Specifically, this invention concerns a one-pot methodology useful to prepare methacrylic derivatives of hyaluronic acid, through the formation of a specific active group on hydroxyl groups of hyaluronic acid, the subsequent substitution of the inserted active group with ethylenediamine and finally, the reaction with methacrylic anhydride. The obtained methacrylic hyaluronic acid derivatives are used to prepare hydrogels through irradiation and loaded with exogenous enzymes selected in the group consisting of prolyl endopeptidase (PEP) and endoprotease (EP). The ability of prepared hydrogels to allow the enzyme release, as active form in simulated gastrointestinal fluids is proved.

9 Claims, 6 Drawing Sheets

HYDROGELS OF METHACRYLIC HYALURONIC ACID DERIVATIVES FOR ORAL ENZYME THERAPY IN CELIAC DISEASE

CROSS REFERENCE TO RELATED APPLICATIONS

The present application claims priority to PCT International Application No. PCT/EP2015/059941 filed on May 6, 2015, which application claims priority to Italian Patent Application No. FI2014A000106 filed May 7, 2014, the entirety of the disclosures of which are expressly incorporated herein by reference.

STATEMENT RE: FEDERALLY SPONSORED RESEARCH/DEVELOPMENT

Not Applicable.

FIELD OF THE INVENTION

The present invention relates to a pharmaceutical composition comprising hyaluronic acid derivatives hydrogels loaded with, at least one exogenous enzyme, said enzyme selected in the group consisting of prolyl endopeptidase (PEP), endoprotease (EP) and combination thereof; said composition intended for the oral treatment of celiac disease.

STATE OF THE ART

Celiac disease is a small intestinal pathology induced by gluten in genetically susceptible individuals, even if environmental factors are also involved in this complex inflammatory disease.

Gluten is a mixture of gliadins and glutenins, rich in proline and glutamine that are not preferred substrates for enzymes of human gastrointestinal tract. As a consequence, gluten is not totally degraded in humans, with production of metastable immunogenic peptides up to 30-40 aminoacids. In particular, the sequence of □2-gliadin, a representative gluten protein, is cleaved by pepsin in the stomach with formation of large peptides, that in the lumen of small intestine are digested by pancreatic proteases and peptidases of intestinal brush border membrane to single aminoacids, di-, and tri-peptides for absorption. However, the 33-mer sequence persists through digestion to traverse the epithelial barrier, becoming deaminated by transglutaminase 2 (TG2) at select glutamine residues. In the underlying lamina propria, epitopes derived from the deaminated 33-mer show high affinity for human leukocyte antigen (HLA) DQ2. Deaminated gluten peptides-DQ2 complexes on the surface of antigen-presenting cells (APCs) elicit a potent inflammatory response from gluten-specific intestinal T cells, that causes destruction of the intestinal architecture, malabsorption of nutrients, diarrhea and anemia.

The complete gluten-free diet allows the resolution of signs and symptoms of celiac disease in most patient, and to date, is the only treatment for this pathology. Obviously, because of ubiquity of gluten in human diet, this restriction is a difficult experience and is often associated with decreased quality of life. In addition, aliments gluten-free are very expensive, therefore besides the not optimal taste, economic reasons often discourage patients. Unfortunately, a poor patient compliance, voluntary or not, to a strict gluten-free diet causes complications such as osteoporosis, secondary immune disorders, malignancies, etc. that can be associated with increased morbidity and mortality.

Therefore, there is a great need for therapeutic alternatives to the gluten-free diet, including among them, oral administration of exogenous prolyl endopeptidases (PEPs).

Unlike human enzymes of gastrointestinal tract, exogenous PEPs can efficiently hydrolyze proline-rich gluten peptides and then avoid the inflammatory response.

Various PEPs have been proposed at this aim, such as PEP derived from *Flavobacterium meninosepticum* (FM), *Myxococcus xanthus* (MX), *Sphingomonas capsulata* (SC) and *Aspergillus niger* (AN), with different sequence and chain length specificity and stability in acidic medium or in the presence of gastrointestinal proteases (Bethune M T and Khosla C. Oral enzyme therapy for celiac sprue. Methods Enzymol. 2012; 502:241-271).

However, for oral administration of these enzyme is necessary to choose an appropriate formulation that allows both the manufacturing process without alteration of the enzyme and its release in the gastro and/or intestinal tract as an active form and in efficacious dose, preferably in a gradual and constant way over time.

To date there are not in the market oral formulations containing PEPs, but only a few examples in clinical trials, such as the combination branded as ALV003 between PEP SC and EP-B2 (a barley endoprotease) (Tye-Din J A, Anderson R P, Ffrench R A, Brown G J, Hodsman P, Siegel M, Botwick W, Shreeniwas R. The effects of ALV003 pre-digestion of gluten on immune response and symptoms in celiac disease in vivo. Clin Immunol. 2010; 134:289-95).

However, it seems that oral enzyme therapy until now investigated is not be able to sufficiently degrade immunogenic epitopes of a normal daily gluten ingestion amounting to >13 g, but rather to eliminate the detrimental effect of a few hundred milligrams to a few grams of gluten in patients with high gluten sensitivity or refractory celiac disease type 1, or to allow an occasional transgression of gluten-free diet.

Finally, the oral therapy to date proposed likely requires administration of PEPs with every meal in which dietary gluten is intentionally or inadvertently ingested.

There is thus a need in the field for improved release of exogenous PEPs for use in the oral treatment of celiac disease, not suffering the drawbacks of the prior part.

Therefore, this invention has the aim to provide new formulations for oral administration of exogenous enzyme selected in the group consisting of prolyl endopeptidase (PEP) and endoprotease (EP), able to release the enzyme in the active form and efficacious dosage in the gastrointestinal tract and in a gradual way, to allow PEP and/or EP administration to a once-daily dose.

DEFINITIONS AND ABBREVIATIONS

EDA: ethylendiamine
EP: endoprotease
HA: hyaluronic acid
MA: methacrylic anhydride
HA-EDA-MA: hyaluronic acid wherein where at least one hydroxyl group has been functionalised by reaction with ethylenediamine (EDA) and subsequent reaction with methacrylic anhydride (MA)
PEP: prolyl endopeptidase
PEP FM: prolyl endopeptidase derived from *Flavobacterium meninosepticum*
PEP MX: prolyl endopeptidase derived from *Myxococcus xanthus*

PEP SC: prolyl endopeptidase derived from *Sphingomonas capsulata*

PEP AN: prolyl endopeptidase derived from *Aspergillus niger*

SUMMARY OF THE INVENTION

The invention provides a composition comprising at least one exogenous enzyme, said enzyme selected in the group consisting of prolyl endopeptidase (PEP), endoprotease (EP) and combination thereof, said enzyme entrapped in a photocrosslinked methacrylic hyaluronic acid derivatives (HA-EDA-MA) hydrogel, wherein the hyaluronic acid derivatives comprise hyaluronic acid (HA), or a salt thereof, of molecular weight comprised between 50,000 and 1,500,000 Daltons where at least one hydroxyl group, after activation with a carbonating agent chosen between carbonic phenylesters or haloformic phenylesters, has been functionalised by reaction with ethylenediamine (EDA) and subsequent reaction with methacrylic anhydride (MA), preferably by using a one-pot synthesis.

The obtained composition is prepared as gel or freeze dried powder.

The enzyme entrapped in the hydrogel surprisingly resulted to be protected from degradation during the freeze drying process, therefore allowing the production and stable long shelf-life of the composition of the invention as freeze-dried powder form.

A composition according to the invention allows the release of the exogenous enzyme in simulated gastrointestinal fluids in a sustained way and as an active form to detoxify gliadin peptide. A composition according to the invention is therefore suitable for use in the treatment of celiac disease and can be used for preparing conventional oral dosage form, like granulates, capsules or tablets, with enteric coating or not, for oral administration and sustained release of enzymes (PEPs, EPs or combinations thereof) as active form able to detoxify gliadin peptide in celiac patients. Subject-matter of the present invention is therefore also a pharmaceutical oral formulation comprising the composition according to the invention and at least another pharmaceutically acceptable ingredient, said formulation for use in the treatment of celiac disease.

Mucoadhesive properties of the starting polymer, i.e. hyaluronic acid, could allow an adhesion to the mucosa of gastrointestinal tract and a consequent longer permanence time of formulation loaded with enzymes (PEPs, EPs or combinations thereof) in the site where gliadin peptide must be detoxified.

Further object of the invention is a process for preparing methacrylic hyaluronic acid derivatives where hydroxyl groups of hyaluronic acid are functionalized with ethylenediamine and then with methacrylic anhydride, said process being a one-pot process.

DETAILED DESCRIPTION OF THE INVENTION

HA-EDA-MA derivatives according to the invention show a functionalization degree in EDA and MA comprised between at least one hydroxyl group and the whole hydroxyl groups of hyaluronic acid.

HA-EDA-MA derivatives can be photocrosslinked, by way of photoirradiation at a wavelength in the range 180-800 nm, in aqueous solution at a concentration between 1% w/v and 20% w/v and in the presence of at least one exogenous enzyme, preferably a PEP, in a concentration between 1 mU/mg and 100 U/mg of polymer.

HA-EDA-MA derivatives can be photocrosslinked, by way of photoirradiation at a wavelength in the range 180-800 nm, in a concentration between 1% w/v and 20% w/v and then loaded through contact of obtained hydrogels with a solution of at least one exogenous enzyme, preferably a PEP, with a concentration between 1 mU/mg and 100 U/mg of polymer. HA-EDA-MA derivatives can be photocrosslinked in aqueous medium, preferably by way of UV irradiation at a 366 nm wavelength in the presence of exogenous enzyme, preferably prolyl endopeptidases (PEP).

In a composition according to the invention the enzyme can be a PEP or an EP derived from a single microorganism or it can be a combination of PEPs and/or EPs derived from different microorganisms or produced by way of biotechnology method; any PEP or EP known in the art and combination thereof are suitable for being entrapped in a hydrogel, according to the invention.

PEP can also be prepared by recombinant technique in *E. coli* as described in Bethune et al. Methods Enzymol. 2012, 502, 241-271 and notes therein.

According to the invention, preferably PEP is derived from a microorganism selected in the group consisting of *Flavobacterium meningosepticum* (FM), *Myxococcus xanthus* (MX), *Sphingomonas capsulata* (SC) or *Aspergillus niger* (AN).

According to the invention preferably EP is a barley EP, particularly preferred is EP-B2.

Preferably, according to the invention, said enzyme is entrapped in the hydrogel, in gel form, in a concentration between 1 mU/mg and 100 U/mg of polymer.

HA-EDA-MA hydrogels loaded with enzymes can be produced as gels.

HA-EDA-MA hydrogels loaded with enzymes can be produced as freeze dried powder.

Freeze drying can be performed both in the absence or in the presence of cryprotectants, in a concentration between 0.1 and 10% w/w respect to the weight of polymer; said cryoprotectant is preferably trehalose.

HA-EDA-MA hydrogels loaded with PEPs (in particular PEP FM), according to the invention, have been tested in release assays of PEPs in simulated gastrointestinal fluids after their storage for different times (until six months from preparation) and at different temperatures (from −20 to 37° C.).

In a previous patent (Giammona, G., Palumbo, F. S., Pitarresi. G., Method to produce hyaluronic acid functionalized derivatives and formation of hydrogels thereof. WO 2010/061005 A1), the synthesis of HA-EDA-MA has been reported, but involved the initial production of HA-EDA derivatives, that after isolation and purification are employed for further reaction with MA, therefore a two-pot synthesis has been reported.

On the contrary in the present invention, one-pot synthesis is claimed that allows directly the production of HA-EDA-MA derivatives without the isolation of HA-EDA derivatives.

Then it is a further subject-matter of this invention a procedure, preferably one-pot, for the production of methacrylic hyaluronic acid derivatives said procedure comprising the following steps:

(a) contacting a hyaluronic acid (HA) salt in polar aprotic solvent with a carbonating agent chosen between carbonic phenylesters or haloformic phenylesters to obtain the activation of at least one hydroxyl group of HA, wherein said HA is in form of a salt soluble in said polar aprotic organic solvent;

(b) contacting the activated HA salt obtained from the step (a) with ethylenediamine (NH2-CH2-CH2-NH2, indicated as EDA), to obtain, by way of nucleophilic substitution, HA-EDA;

(c) contacting HA-EDA obtained from the step (b) with methacrylic anhydride (indicated as MA), to obtain, by way of nucleophilic substitution, HA-EDA-MA;

wherein, preferably all the above steps are performed in the same vessel.

The hyaluronic acid salt soluble in organic solvents are preferably chosen between the tetrabutylammonic salt (indicated as TBA) or the cetyltrimethylammonium salt (indicated as CTA).

The polar aprotic organic solvent employed for the functionalization reactions is preferably chosen between dimethylsulfoxide, dimethylformamide, dimethylacetamide and mixtures thereof.

The carbonating agent employed in step (a) can preferably be the bis(4-nitrophenyl carbonate) (a carbonyl phenyl ester) and/or a chloro nitrophenyl carbonate.

The step (c) is preferably carried out in the presence of a catalyst chosen between diethylamine, triethylamine, dimethylaminopyridine and mixtures thereof.

All steps are preferably carried out at temperatures between 5 and 60° C.

The functionalization degree in EDA and MA groups linked to HA can vary from only one hydroxyl group to the whole hydroxyl groups of HA and it depends (in a manner directly proportional) upon the amount of carbonilating agent used in the above described process. Preferably the functionalization degree varies between 5 and 95%, more preferably between 20 and 80%.

According to a further aspect, the present invention, deals with HA-EDA-MA derivatives having a molecular weight in the range of 50,000-1,500,000 Dalton obtainable from process as above described.

Hereinafter is presented a structural formula of HA-EDA-MA which is to be intended as just representative of the type of functionalization (covalent bonding) which occurs to a HA hydroxyl group when subjected to the above described process.

The structure hereinafter reported is not to be intended as representative of the funtionalization degree which, as stated above, is instead directly proportional to the amount of reactive carbonilating agent, used in the above process.

In particular, the type of functionalization of HA-EDA-MA derivatives could be represented by the following structure describing two consecutive disaccharide units of the starting hyaluronic acid, wherein at least one hydroxyl group has been functionalised.

HA-EDA-MA

According to a further aspect, the present invention, deals with crosslinked hydrogels obtained from the above described products, i.e. HA-EDA-MA derivatives, employing a photocrosslinking procedure, where the concentration of the mentioned functionalized derivatives in aqueous or organic solution is comprised between 1% w/v and 20% w/v. Preferably hydrogels are obtained by irradiating with wavelengths comprised between 180 and 800 nm, with or without radical photoinitiator, with irradiation time comprised between 5 min and 10 h.

Such hydrogels can be obtained also by □-ray, microwave irradiation or by other ionizing radiations.

Such photocrosslinking can occurs also in the presence of appropriate additives as acrylic and methacrylic monomers, polyethylenglycole methacrylates and acrylates, both mono and polyfunctional, or in the presence of other additives employed to change or improve plasticity, hardness, hydrophilic and lipophilic character.

According to a further aspect, the present invention deals with the production of hydrogels of HA-EDA-MA obtained through photoirradiation and loaded with exogenous prolyl endopeptidases (PEPs) with a concentration of enzyme between 1 mU/mg and 100 U/mg of polymer, during and/or after irradiation process.

According to a specific aspect, the present invention deals with the production of HA-EDA-MA derivatives photocrosslinked in aqueous medium, preferably at 366 nm for 10 min, in the presence of exogenous prolyl endopeptidases (PEPs), preferably PEP derived from *Flavobacterium meningosepticum* (FM) with a concentration of enzyme between 1 mU/mg and 100 U/mg of polymer.

HA-EDA-MA hydrogels loaded with PEPs are produced both as gels or freeze dried powders in the absence or in the presence of cryprotectants, with a concentration between 0.1 and 10% w/w respect to the weight of polymer.

The obtained hydrogels loaded with PEPs were used for release experiments in simulated gastrointestinal fluids both just after their production and after their storage for different times (until six months from preparation) and at different temperatures (from −20 to 37° C.).

Experiment results demonstrate that:

PEP FM alone dissolved in phosphate buffer solution pH 7.2, loses gradually its activity with time, even if stored at low temperature, e.g. 4° C.

PEP FM alone dissolved in phosphate buffer solution pH 7.2, loses totally its activity after freeze drying of the solution, also in the presence of cryoprotectants;

PEP FM alone dissolved in phosphate buffer solution pH 7.2 and photoirradiated at 366 nm for 10 min, maintains its activity during photoirradiation, but it loses totally its activity after freeze drying of the solution, also in the presence of cryoprotectants;

PEP FM dissolved in phosphate buffer solution pH 7.2 in the presence of HA-EDA-MA derivative, and photoirradiated at 366 nm for 10 min, maintains its activity also after freeze drying, both in the absence and in the presence of cryoprotectants;

Hydrogels of HA-EDA-MA loaded with PEP FM during photoirradiation and recovered as gels, if analyzed just after their preparation, are able to release in a sustained way about 70% of enzyme in simulated intestinal fluid pH 7.2, as active form until 24 h. The amount of PEP FM that remains into HA-EDA-MA gels, maintains totally its activity.

Hydrogels of HA-EDA-MA loaded with PEP FM during photoirradiation and recovered as gels, if analyzed after storage at 4° C. for 10 days, are able to release in a sustained way about 60% of enzyme in simulated intestinal fluid pH 7.2, as active form until 24 h and only a partial loss in activity occurs (about 20%).

Hydrogels of HA-EDA-MA loaded with PEP FM during photoirradiation in the absence of cryoprotectants, and recovered as freeze dried powders, if analyzed just after their preparation, are able to release in a sustained way about 70% of enzyme in simulated intestinal fluid pH 7.2, as active form until 24 h. The amount of PEP FM that remains into HA-EDA-MA hydrogels, maintains totally its activity.

Hydrogels of HA-EDA-MA loaded with PEP FM during photoirradiation in the absence of cryoprotectants, and recovered as freeze dried powders, if analyzed after storage at 4° C. or −20° C. for 10 days, are able to release in a sustained way about 50% of enzyme in simulated intestinal fluid pH 7.2, as active form until 24 h and only a partial loss in activity occurs (about 30%). This is very good result since PEP FM alone, i.e. in the absence of HA-EDA-MA hydrogel, loses totally its activity following freeze drying.

Hydrogels of HA-EDA-MA loaded with PEP FM during photoirradiation in the presence of trehalose (as an example of cryoprotectant) at 1.5% w/w respect to the weight of polymer, and recovered as freeze dried powders, if analyzed just after their preparation, are able to release in a sustained way about 60% of enzyme in simulated intestinal fluid pH 7.2, as active form until 24 h. The amount of PEP FM that remains into HA-EDA-MA hydrogels, maintains totally its activity.

If these samples are stored at 4° C. for 10 days, they are still able to release in a sustained way about 50% of PEP FM in simulated intestinal fluid pH 7.2, as active form until 24 h and only a partial loss in activity occurs (about 30%).

If these samples are stored for at −20° C. for 10 days, they are still able to release in a sustained way about 50% of PEP FM in simulated intestinal fluid pH 7.2, as active form until 24 h and PEP FM maintains totally its activity.

Hydrogels of HA-EDA-MA loaded with PEP FM during photoirradiation in the presence of trehalose (as an example of cryoprotectant) at 3% w/w respect to the weight of polymer, and recovered as freeze dried powders, if analyzed just after their preparation, are able to release in a sustained way about 50% of enzyme in simulated intestinal fluid pH 7.2, as active form until 24 h. The amount of PEP FM that remains into HA-EDA-MA hydrogels, maintains totally its activity.

If these samples are stored 4° C. or −20° C. for 1 and 2 months, they are still able to release in a sustained way about 50% of PEP FM in simulated intestinal fluid pH 7.2, as active form until 24 h and PEP FM maintains totally its activity.

Therefore, according to the above results, composition according to the invention prepared through photoirradiation of HA-EDA-MA hydrogels in the presence of PEP FM and a cryoprotector with an appropriate concentration, are able to protect totally the enzyme activity from freeze drying process.

The PEP FM loaded into HA-EDA-MA hydrogels recovered as freeze dried powders maintains totally its activity during storage at different times and temperature, and it is released as active form in simulated intestinal fluid pH 7.2 until 24 h from HA-EDA-MA hydrogels.

Following the same approach employed for loading PEP FM, the present invention deals with HA-EDA-MA hydrogels loaded with other exogenous enzyme selected in the group consisting of prolyl endopeptidase (PEP), like PEP from *Myxococcus xanthus* (MX), PEP from *Sphingomonas capsulata* (SC) or PEP from *Aspergillus niger* (AN), and endoprotease (EP), all employed alone or in combination with PEP FM or between them or with other enzymes.

In conclusion HA-EDA-MA hydrogels are able:

to protect the loaded enzymes from freeze drying process;

to protect the loaded enzymes from alteration during the storage of freeze dried powders, overall in the presence of cryoprotectants;

to allow enzymes release in simulated gastric fluid (for acid-active enzymes) and in simulated intestinal fluid (for all enzymes) as active form and in a sustained way, to be used to prepare conventional oral dosage form, like granulates, capsules and tablets, with enteric coating or not, for oral administration and release of enzymes as active form able to detoxify gliadin peptide in celiac patients.

The invention will be further illustrated by means of the following examples, intended to assist in understanding the invention and not to be construed as specifically limiting the invention described and claimed herein.

EXPERIMENTAL SECTION

Example 1

Preparation of HA-EDA-MA Derivative by One-Pot Synthesis 1 g of tetrabutylammonium salt of hyaluronic acid (HA-TBA), prepared by hyaluronic acid solution neutralization using tetrabutylammonium hydroxide solution, has been dissolved in 90 ml of anhydrous dimethylsulfoxide (DMSO) (weight-average molecular weight of hyaluronic acid 260 kDa).

The suitable amount of bis(4-nithrophenyl) carbonate (4-NPBC) chosen in a way to obtain a molar ratio 4-NPBC/Repeating Units of HA-TBA equal to 0.5, has been dissolved in 10 ml of anhydrous DMSO; this solution has been added drop by drop to the HA-TBA solution at 40° C. under stirring. After 4 h, 175 μl of ethylendiamine (EDA) have been added drop by drop and the solution was left at 40° C. for other 3 h.

An appropriate volume (900 μl) of methacrylic anhydride (MA) to obtain a eight fold molar excess compared to the moles of amino groups on the HA-TBA-EDA, has been added, then 105 μl of catalyst triethylamine (TEA) has been added and the final solution was left for 24 h at 40° C.

The work-up of the reaction has been accomplished by first adding 10 ml of a NaCl saturated solution and the mixture has been left 30 min under stirring at room temperature. Then, the reaction solution has been precipitated into ethanol and the product has been washed several times with a solution of ethanol/bidistilled water (9:1) until a product without reaction intermediates and NaCl has been obtained. The obtained solid has been named as HA-EDA-MA derivative. Scheme 1 shows the one-pot procedure used to prepare HA-EDA-MA derivative.

Scheme 1. Reaction of functionalization of tetrabutylammonium salt of hyaluronic acid (HA-TBA) with ethylenediamine (EDA) and methacrylic anhydride (MA) to obtain HA-EDA-MA derivative by one-pot procedure

HA-EDA-MA

The HA-EDA-MA derivative has been characterized by $^1$H-NMR (see FIG. 1), showing the following peaks (D$_2$O): δ 1.9 (s, —CO—CH═CH—CH$_3$); δ 2.0 (s, —NH—CO—CH$_3$); δ 5.5 and 5.7 (m, —CO—CH═CH—CH$_3$).

Figure 1:
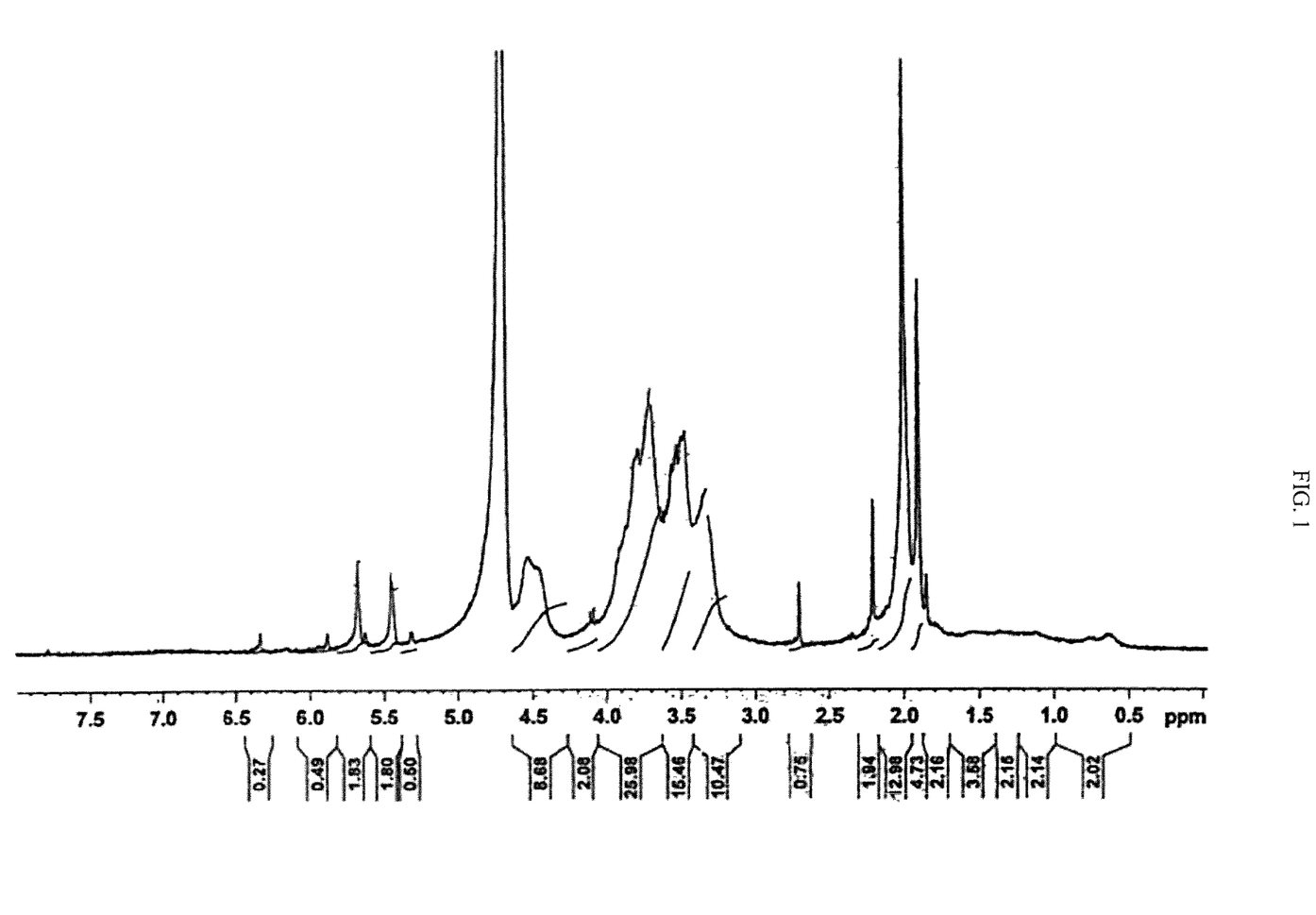
FIG. 1 shows the 1H-NMR spectrum of HA-EDA-MA derivative

The functionalization degree has been evaluated by comparing the areas of peaks a δ 5.5 and 5.7 attributable to the vinyl protons of the methacrylic group with the area at δ 1.9 attributable to the methyl group of the N-acetylglucosamine portion of HA repetitive units. The functionalization degree in methacrylic groups linked to the repetitive units of HA-EDA resulted to 50% mol/mol, the peak belonging to the amino free groups of EDA is absent i.e. at δ 3.1 (m, CO—NH—CH$_2$—CH$_2$—NH$_2$), so all amino groups have been derivatized with methacrylic anhydride.

Example 2

Figure 2:
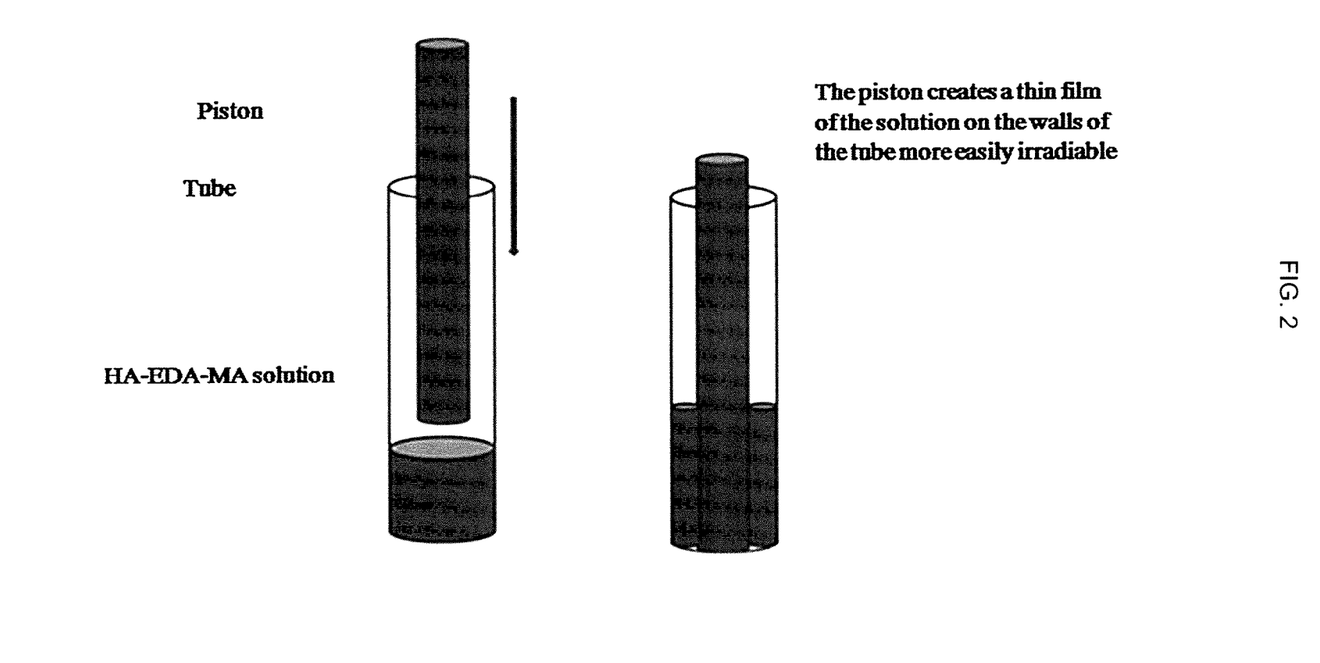
FIG. 2 shows the scheme of Pyrex tube-piston system used for the photoirradiation of HA-EDA-MA solutions.

Photocrosslinking of HA-EDA-MA Derivative 30 mg of HA-EDA-MA derivative obtained following the Example 1, have been dissolved in 500 µl of 0.05 M phosphate buffer solution pH 7.2, at room temperature, in order to have a final concentration equal to 6% w/v and degassed under vacuum. Then, the solution has been placed in Pyrex tube and irradiated using a Rayonet photoreactor UV at a wavelength of 366 nm for 10 min (see FIG. 2). After this time, obtained hydrogel has been recovered as gel or freeze dried to obtain a powder.

Example 3

Evaluation of PEP FM Activity

Activity of PEP derived from *Flavobacterium meningosepticum* (FM) has been measured through a colorimetric assay in which the enzyme reacts with its specific substrate i.e. carbobenzoxy-Gly-Pro-p-nitroanilide (Z-Gly-Prp-pNA).

In particular, 0.25 ml of 2 mM Z-Gly-Pro-pNA in 40% dioxane have been mixed with 1.0 ml of 0.1 M phosphate buffer solution pH 7.2 and the solution has been preincubated for 5 min at 30° C. After this time, 0.1 ml of enzyme in 0.05 M phosphate buffer solution pH 7.2 has been added and after incubation for 10 min at 30° C., the reaction has been stopped by addition of 2.0 ml of Triton-X100 solution (10 g Triton-X100/95 ml 1M acetate buffer, pH 4.0).

The absorbance of the resulting product has been measured at 380 nm.

One unit of the enzyme activity is defined as the enzyme activity which produces 1 µmol p-nitroaniline per min at 30° C., pH 7.2, from Z-Gly-Pro-pNA.

Example 4

Stability of PEP FM in Phosphate Buffer Solution pH 7.2 as a Function of Time

Figure 3:
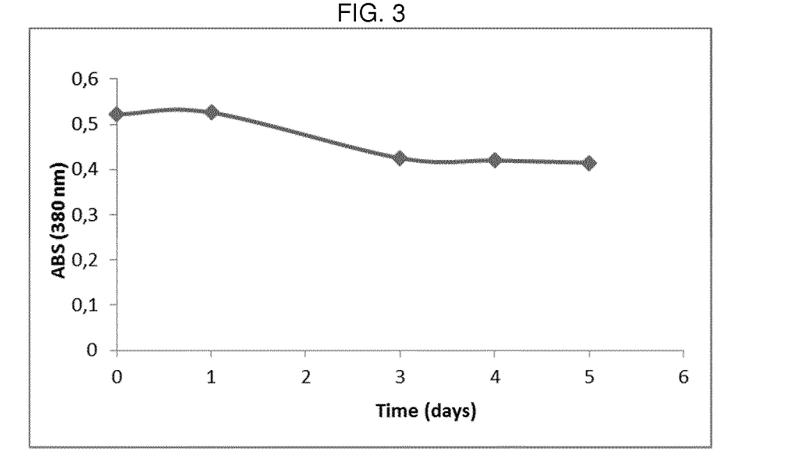
FIG. 3 shows the stability of PEP FM in phosphate buffer solution pH 7.2, expressed as a measure of the absorbance (ABS) at 380 nm of the substrate solutions (Z-Gly-Pro-pNA) processed with the enzyme after storage at 4° C. up to 5 days.

Aliquots (1.0 ml) of 0.2 U/ml of PEP FM in 0.05 M phosphate buffer solution pH 7.2 have been prepared and kept in a refrigerator a 4° C. until 5 days in order to assess their stability over time. After 1 2, 3, 4 and 5 day, the activity of the enzyme has been evaluated through the colorimetric assay as reported in the Example 3. Each experiment has been performed in triplicate. Results are shown in FIG. 3.

Example 5

Freeze Drying of PEP FM in Phosphate Buffer Solution pH 7.2 and Evaluation of its Activity One ml of 0.2 U/ml of PEP FM in 0.05 M phosphate buffer solution pH 7.2 in the absence or in the presence of trehalose (7.5 µg/ml or 15 µg/ml) has been freeze-dried. Then the activity of the enzyme has been evaluated through the colorimetric assay as reported in the Example 3. Each experiment has been performed in triplicate. In all cases, no activity was found.

Example 6

Photoirradiation of PEP FM in Phosphate Buffer Solution pH 7.2 and Evaluation of its Activity One ml of 0.2 U/ml of PEP FM in 0.05 M phosphate buffer solution pH 7.2 has been photoirradiated at a wavelength equal to 366 nm for different times (from 1 to 20 min).

After each irradiation time, the activity of the enzyme has been evaluated through the colorimetric assay as reported in the Example 3.

Figure 4:
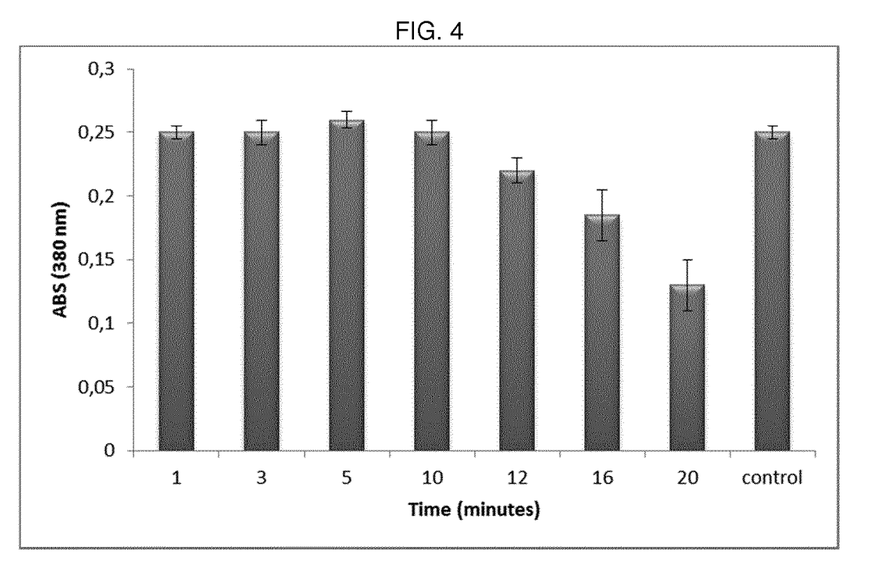
FIG. 4 shows PEP FM activity expressed as a measure of the absorbance (ABS) at 380 nm of the substrate solutions (Z-Gly-Pro-pNA) processed with the enzyme after its irradiation at 366 nm for different times.

The activity assay was also performed on non-irradiated enzyme solutions, used as a positive control. Each experiment has been performed in triplicate. Results are shown in FIG. 4.

Example 7

Freeze Drying of PEP FM in Phosphate Buffer Solution pH 7.2 after its Photoirradiation and Evaluation of its Activity One ml of 0.2 U/ml of PEP FM in 0.05 M phosphate buffer solution (PBS) pH 7.2 has been photoirradiated at a wavelength equal to 366 nm for 10 min.

Irradiated solution has been freeze-dried and the activity of the enzyme has been evaluated through the colorimetric assay as reported in the Example 3.

The experiment has been performed in triplicate and in all cases no activity has been found.

Example 8

Freeze Drying of PEP FM in Phosphate Buffer Solution pH 7.2 after its Photoirradiation in the Presence of Trehalose and Evaluation of its Activity 200 µl of 0.2 U/ml PEP FM in 0.05 M phosphate buffer solution pH 7.2 have been mixed with 800 µl of 15 µg/ml trehalose in 0.05 M phosphate buffer solution pH 7.2. This solution has been photoirradiated at a wavelength equal to 366 nm for 10 min.

The irradiated solution has been freeze-dried and the activity of the enzyme has been evaluated through the colorimetric assay as reported in the Example 3.

The experiment has been performed in triplicate and in all cases no activity has been found.

Example 9

Preparation of HA-EDA-MA Gel Loaded with PEP FM

Thirty mg of HA-EDA-MA derivative have been dissolved in 400 µl of 0.05 M phosphate buffer solution pH 7.2. The solution has been degassed under vacuum and then 100 µl of 0.4 U/mg PEP FM in 0.05 M phosphate buffer solution pH 7.2 has been added. In this was the final polymer concentration has been equal to 6% w/v. The solution has been photoirradiated at a wavelength equal to 366 nm for 10 min.

The obtained HA-EDA-MA gel loaded with PEP FM has been analyzed just after its preparation or after storage at 4° C. for 10 days.

Each experiment has been performed in triplicate.

Example 10

Preparation of HA-EDA-MA Hydrogel as Freeze Dried Powder Loaded with PEP FM

HA-EDA-MA hydrogel loaded with PEP FM at 0.4 U/mg of polymer has been prepared as reported in the Example 9.

After photoirradiation, the obtained hydrogel has been freeze-dried, then analyzed just after its preparation or after storage for 10 days at 4° C. or −20° C.

Each experiment has been performed in triplicate.

Example 11

Preparation of HA-EDA-MA Hydrogel as Freeze Dried Powder Loaded with PEP FM in the Presence of 1.5% w/w of Trehalose Thirty mg of HA-EDA-MA derivative have been dissolved in a mixture of 350 µl of 0.05 M phosphate buffer solution pH 7.2 and 100 µl of 4.5 mg/ml trehalose in 0.05 M phosphate buffer solution pH 7.2. The solution has been degassed under vacuum and then 50 µl of 0.4 U/mg PEP FM in 0.05 M phosphate buffer solution pH 7.2 have been added. The solution has been photoirradiated at a wavelength equal to 366 nm for 10 min.

After photoirradiation, the obtained hydrogel has been freeze-dried, then analyzed just after its preparation or after storage for 10 days at 4° C. or −20° C.

Each experiment has been performed in triplicate.

Example 12

Preparation of HA-EDA-MA Hydrogel as Freeze Dried Powder Loaded with PEP FM in the Presence of 3% w/w of Trehalose Thirty mg of HA-EDA-MA derivative have been dissolved in a mixture of 350 µl of 0.05 M phosphate buffer solution pH 7.2 and 100 µl of 9 mg/ml trehalose in 0.05 M phosphate buffer solution pH 7.2. The solution has been degassed under vacuum and then 50 µl of 0.4 U/mg PEP FM in 0.05 M phosphate buffer solution pH 7.2 have been added. The solution has been photoirradiated at a wavelength equal to 366 nm for 10 min.

After photoirradiation, the obtained hydrogel has been freeze-dried, then analyzed just after its preparation or after storage for 10 days, 1 or 2 months at 4° C. or −20° C.

Each experiment has been performed in triplicate.

Example 13

Release Studies in Simulated Intestinal Fluid pH 7.2 from Sample of Example 9

Aliquots (15 mg) of PEP FM loaded HA-EDA-MA gel have been placed in vials containing 10 ml of simulated intestinal fluid pH 7.2 for 24 h (100 rpm, 37° C.). At predetermined time intervals, 0.15 ml of release medium has been withdrawn and analyzed by the assay for the determination of the enzyme activity as described in the Example 3. An equal volume of fresh medium has been added and sink conditions have been maintained throughout the experiment. The amount of the enzyme has been determined by using a calibration curve (y=1.5836 x+0.0537, $r^2$=0.9981).

Each experiment has been performed in triplicate.

The determination of enzyme amount that remains into HA-EDA-MA gel after 24 h, has been performed by using the assay for the determination of enzyme activity, but in this case the substrate Z-Gly-Pro-pNA has been placed directly in contact with the gel.

In particular, 15 mg of gel used for the release studies have been added with 0.5 ml of simulated intestinal fluid pH 7.2 and 4.0 ml of 0.1 M phosphate buffer solution pH 7.2, then the sample has been incubated at 100 rpm, 37° C. for 24 h. After this time, 1.25 ml of 2 mM Z-Gly-Pro-pNA in 40% dioxane has been mixed with 1.0 ml of 0.1 M phosphate buffer solution pH 7.2 and the resulting solution has been preincubated for 5 min at 30° C. then it has been added to the gel and after incubation for 10 min at 30° C., the reaction has been stopped by addition of 20 ml of Triton-X100 solution (10 g Triton-X100/95 ml 1M acetate buffer, pH 4.0).

The absorbance of the resulting product has been measured at 380 nm.

Figure 5:
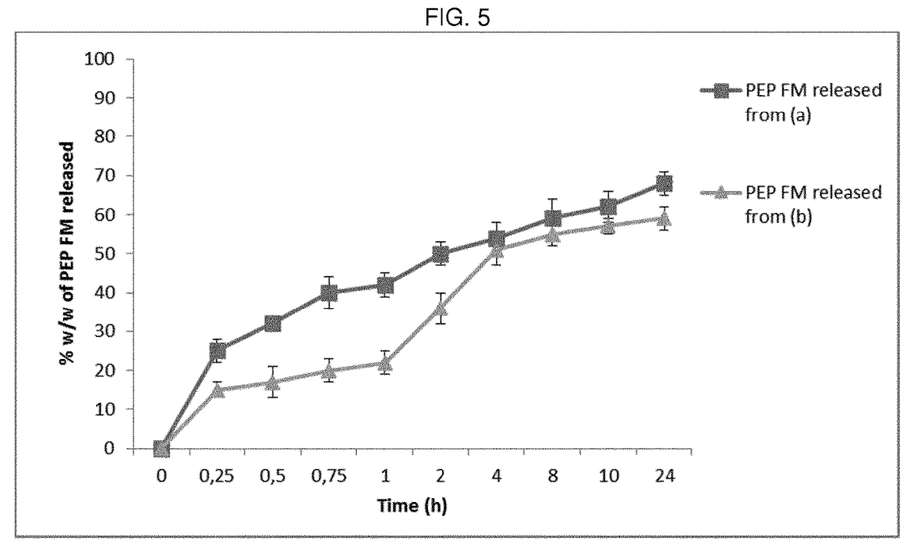
FIG. 5 shows PEP FM released from HA-EDA-MA gels analyzed just after their preparation (a) and after storage at 4° C. for 10 days (b). Release studies were performed in simulated intestinal fluids, pH 7.2 from 0 to 24 h.

Each experiment has been performed in triplicate. Results of release experiments are shown in FIG. 5.

Example 14

Release Studies in Simulated Intestinal Fluid pH 7.2 from Sample of Example 10

Figure 6:
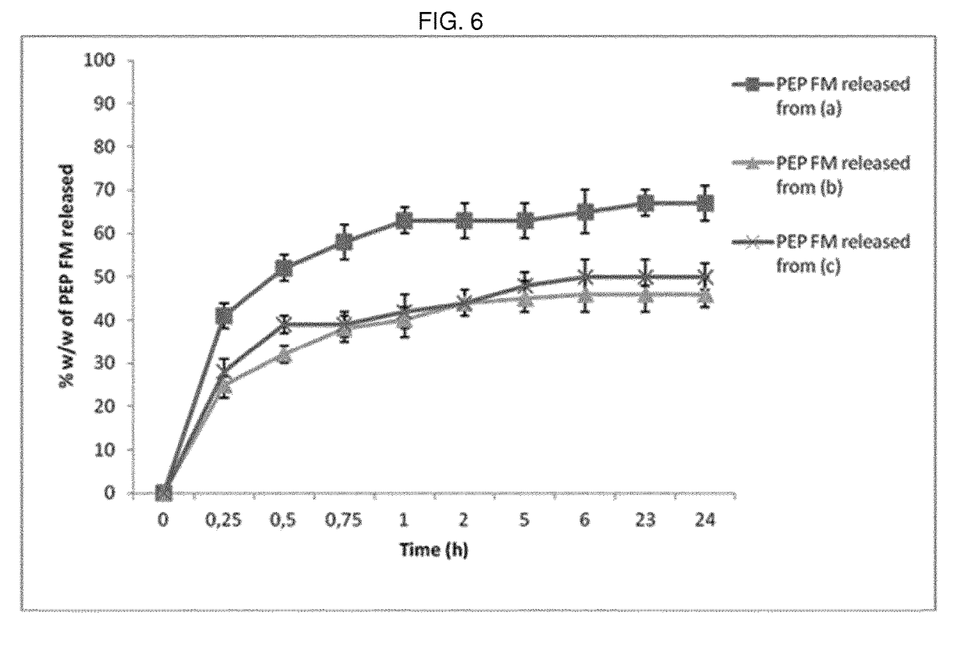
FIG. 6 shows PEP FM released from HA-EDA-MA freeze dried powders analyzed just after their preparation (a), after storage at 4° C. for 10 days (b) and after storage at −20° C. for 10 days (c). Release studies were performed in simulated intestinal fluids, pH 7.2 from 0 to 24 h.

Release studies of PEP FM from HA-EDA-MA hydrogel as freeze dried powder loaded with PEP FM in the absence of cryoprotectant (Example 10) have been performed as described in the Example 13. Results of release experiments are shown in FIG. 6.

Example 15

Release Studies in Simulated Intestinal Fluid pH 7.2 from Sample of Example 11

Figure 7:
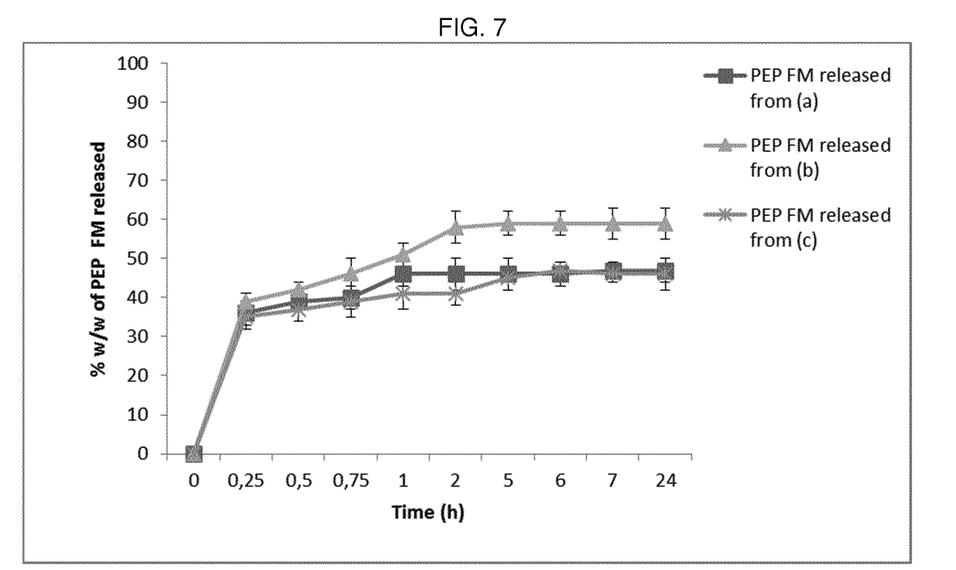
FIG. 7 shows PEP FM released from HA-EDA-MA freeze dried powders in the presence of 1.5 w/w of trehalose analyzed just after their preparation (a), after storage at 4° C. for 10 days (b) and after storage at −20° C. for 10 days (c). Release studies were performed in simulated intestinal fluids, pH 7.2 from 0 to 24 h.

Release studies of PEP FM from HA-EDA-MA hydrogel as freeze dried powder loaded with PEP FM in the presence trehalose (1.5% w/w) (Example 11) have been performed as described in the Example 13. Results of release experiments are shown in FIG. 7.

Example 16

Release Studies in Phosphate Buffer Solution pH 7.2 from Sample of Example 12

Figure 8:
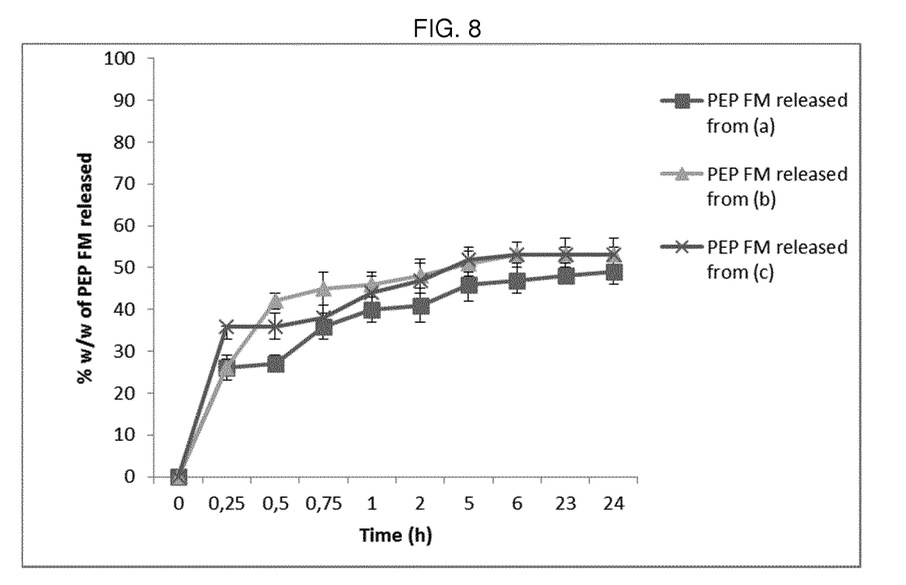
FIG. 8 shows PEP FM released from HA-EDA-MA freeze dried powders in the presence of 3% w/w of trehalose analyzed just after their preparation (a), after storage at 4° C. for 10 days (b) and after storage at −20° C. for 10 days (c). Release studies were performed in simulated intestinal fluids, pH 7.2 from 0 to 24 h.
Figure 9:
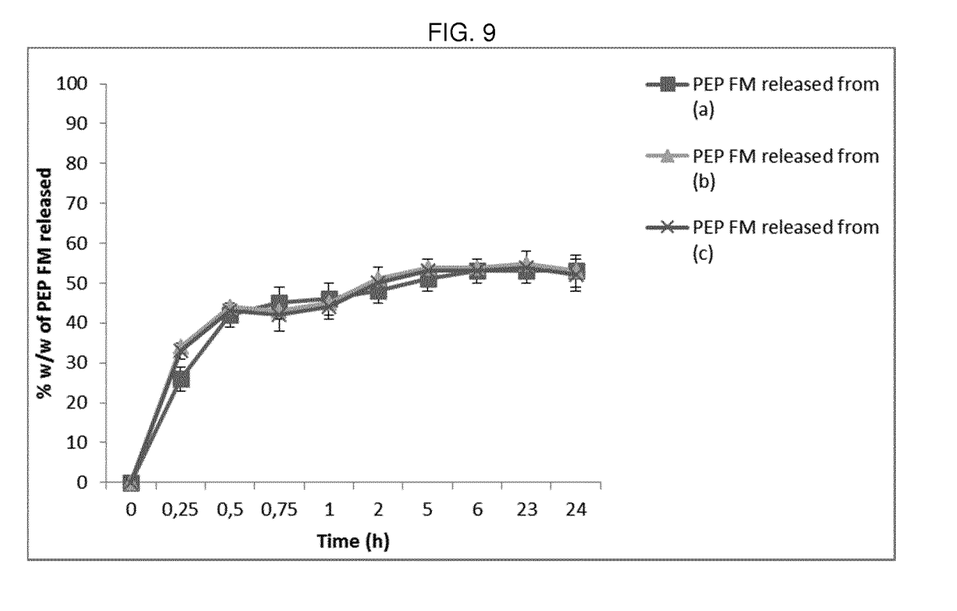
FIG. 9 shows PEP FM released from HA-EDA-MA freeze dried powders in the presence of 3% w/w of trehalose analyzed after storage at 4° C. for 10 days (a), 1 month (b) and 2 months (c). Release studies were performed in simulated intestinal fluids, pH 7.2 from 0 to 24 h.
Figure 10:
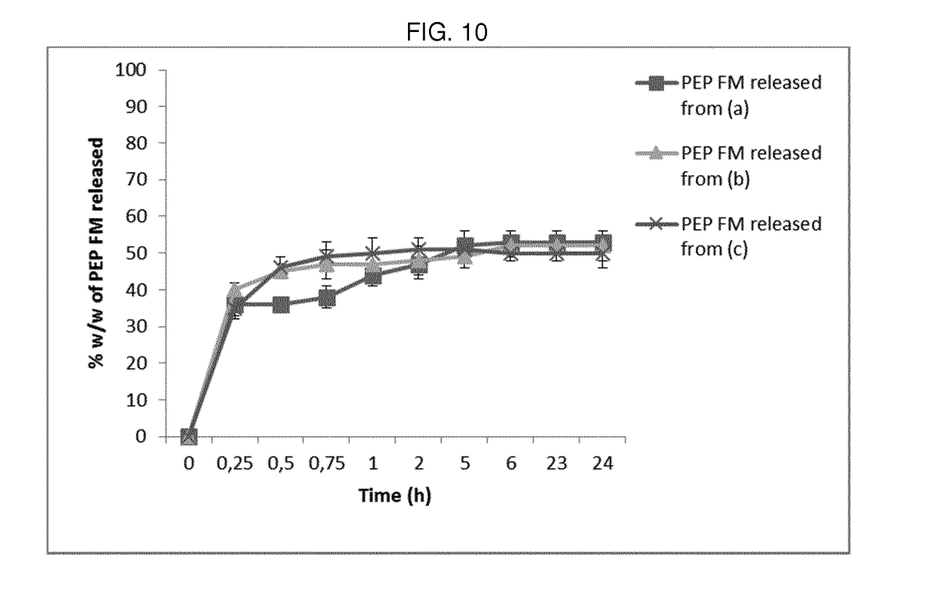
FIG. 10 shows PEP FM released from HA-EDA-MA freeze dried powders in the presence of 3% w/w of trehalose analyzed after storage at −20° C. for 10 days (a), 1 month (b) and 2 months (c). Release studies were performed in simulated intestinal fluids, pH 7.2 from 0 to 24 h.

Release studies of PEP FM from HA-EDA-MA hydrogel as freeze dried powder loaded with PEP FM in the presence trehalose (3% w/w) (Example 12) have been performed as described in the Example 13. Results of release experiments are shown in FIGS. 8, 9 and 10.

The invention claimed is:

1. A composition comprising:
   at least one exogenous enzyme, said enzyme being selected from the group consisting of prolyl endopeptidase (PEP), endoprotease (EP) and combinations thereof, said enzyme in a concentration between 1 mU/mg and 100 U/mg being entrapped in an HA-EDA-MA hydrogel; and
   trehalose in a concentration between 0.1 and 10% w/w with respect to the weight of the HA-EDA-MA hydrogel;
   wherein the HA-EDA-MA hydrogel is formed by photocrosslinking HA-EDA-MA derivatives;
   wherein the HA-EDA-MA derivatives is formed from hyaluronic acid (HA) or a salt thereof, having a molecular weight between 50,000 and 1,500,000 Daltons, and is formed via activation of at least one hydroxyl group of HA with a carbonating agent chosen between carbonic phenylesters and haloformic phenylesters followed by functionalization of the activated hydroxyl group by reaction with ethylenediamine (EDA) and subsequent reaction with methacrylic anhydride (MA); and wherein the composition is in the form of a freeze dried powder.

2. The composition according to claim 1, wherein the concentration of trehalose is 3% w/w with respect to the weight of the HA-EDA-MA hydrogel.

3. The composition according to claim 1 wherein said enzyme comprises PEP, and wherein said PEP is derived from a microorganism selected from the group consisting of *Flavobacterium meningosepticum* (FM), *Myxococcus xanthus* (MX), *Sphingomonas capsulata* (SC) or *Aspergillus niger* (AN) or combinations thereof.

4. A method of treating celiac disease, said method comprising administering to a subject in need thereof a composition according to claim 1.

5. A pharmaceutical formulation comprising a composition according to claim 1, said formulation being adapted for oral administration.

6. A process for preparing a composition according to claim 1, comprising photocrosslinking HA-EDA-MA derivatives, by way of photoirradiation at a wavelength in the range of 180-800 nm, in aqueous solution at a concentration between 1% w/v and 20% w/v wherein said photocrosslinking is performed in the presence of at least one exogenous enzyme, the at least exogenous enzyme being entrapped in the HA-EDA-MA hydrogel having a concentration between 1 mU/mg and 100 U/mg, the HA-EDA-MA hydrogel further including trehalose in a concentration between 0.1 and 10% w/w with respect to the weight of the HA-EDA-MA hydrogel, and freeze drying the HA-EDA-MA hydrogel.

7. The process according to claim 6, comprising preparing HA-EDA-MA derivatives according to the following steps:
   (a) contacting a hyaluronic acid (HA) salt in polar aprotic solvent with a carbonating agent chosen between carbonic phenylesters and haloformic phenylesters to obtain the activation of at least one hydroxyl group of HA, wherein said HA is in form of a salt soluble in said polar aprotic solvent;
   (b) contacting the activated HA salt obtained from the step (a) with EDA, to obtain, by way of nucleophilic substitution, HA-EDA;
   (c) contacting HA-EDA obtained from the step (b) with (MA, to obtain, by way of nucleophilic substitution, HA-EDA-MA.

8. The process according to claim 7, wherein the steps for preparing the HA-EDA-MA derivatives are all performed subsequently in the same vessel.

9. The composition according to claim 1, wherein said enzyme comprises EP, and wherein said EP is a barley endoprotease.

* * * * *